(12) United States Patent
Bandura et al.

(10) Patent No.: US 9,632,079 B2
(45) Date of Patent: Apr. 25, 2017

(54) MOLECULAR CYTOMETRY (71) Applicant: FLUIDIGM CANADA INC., Markham (CA)

(72) Inventors: Dmitry R. Bandura, Aurora (CA); Vladimir I. Baranov, Richmond Hill (CA); Alexander V. Loboda, Thornhill (CA); Olga Ornatsky, Richmond Hill (CA); Scott D. Tanner, Aurora (CA)

(73) Assignee: Fluidigm Canada Inc., Markham (CA)

( * ) Notice: Subject to any disclaimer, the term of this patent is extended or adjusted under 35 U.S.C. 154(b) by 0 days.

(21) Appl. No.: 14/894,287

(22) PCT Filed: May 22, 2014

(86) PCT No.: PCT/CA2014/050474
§ 371 (c)(1),
(2) Date: Nov. 25, 2015

(87) PCT Pub. No.: WO2014/190429
PCT Pub. Date: Dec. 4, 2014

(65) Prior Publication Data
US 2016/0123970 A1 May 5, 2016

Related U.S. Application Data

(60) Provisional application No. 61/827,850, filed on May 28, 2013, provisional application No. 61/827,854, (Continued)

(51) Int. Cl.
*G01N 33/532* (2006.01)
*G01N 15/10* (2006.01)
(Continued)

(52) U.S. Cl.
CPC ... *G01N 33/54366* (2013.01); *G01N 15/1031* (2013.01); *G01N 27/622* (2013.01);
(Continued)

(58) Field of Classification Search
CPC ........... G01N 15/1031; G01N 15/1459; G01N 2015/1006; G01N 27/622; G01N 27/624;
(Continued)

(56) References Cited

U.S. PATENT DOCUMENTS 6,526,096 B2   2/2003  Lainema et al.
7,452,726 B2   11/2008 Chou et al.
(Continued)

FOREIGN PATENT DOCUMENTS

CA   2 466 861 A1   7/2003
CA   2 535 510 A1   3/2005
CA   2 852 043 A1   5/2013

OTHER PUBLICATIONS

International Search Report mailed on Jul. 29, 2014, 9 pages.

*Primary Examiner* — Jennifer Wecker
(74) *Attorney, Agent, or Firm* — Kilpatrick Townsend & Stockton LLP (57) ABSTRACT

The invention relates to methods and devices for molecular cytometry. The molecular cytometer is for use in the analysis of molecular tag labeled particles. In the molecular cytometer, volatile molecular tags attached to the particles, such as cells, are released as groups of molecular tags and ionized by the method of soft ionization to produce corresponding groups of molecular ions. The molecular cytometer has two detectors, one to detect the presence of the groups of molecular ions and the other to detect mobility separated molecular ions. The mobility separated molecular ions are synchronized to correspond with the groups of molecular ions.

20 Claims, 4 Drawing Sheets

Related U.S. Application Data filed on May 28, 2013, provisional application No. 61/827,856, filed on May 28, 2013.

(51) Int. Cl.
| | |
|---|---|
| *H01J 49/00* | (2006.01) |
| *G01N 33/543* | (2006.01) |
| *G01N 27/62* | (2006.01) |
| *G01N 33/483* | (2006.01) |
| *G01N 15/14* | (2006.01) |

(52) U.S. Cl.
CPC ......... *G01N 27/624* (2013.01); *G01N 33/483* (2013.01); *G01N 33/532* (2013.01); *G01N 33/54313* (2013.01); *G01N 15/1404* (2013.01); *G01N 15/1459* (2013.01); *G01N 2015/1006* (2013.01); *G01N 2458/15* (2013.01)

(58) Field of Classification Search
CPC ............... G01N 33/483; G01N 33/532; G01N 33/54313; G01N 33/54366; G01N 15/1404; G01N 2458/15
See application file for complete search history.

(56) References Cited

U.S. PATENT DOCUMENTS

2005/0218319 A1\* 10/2005 Bandura ............ G01N 15/1404
250/288
2008/0046194 A1\* 2/2008 Antonov ............. H01J 49/0036
702/27

\* cited by examiner

FIG. 4

MOLECULAR CYTOMETRY

CROSS-REFERENCE TO RELATED APPLICATIONS

This application is a US National Phase entry of PCT Patent Application No. PCT/CA2014/050474, filed on May 22, 2014, which claims benefit of U.S. provisional application No. 61/827,850 filed May 28, 2013; 61/827,854 filed May 28, 2013; and 61/827,856 filed May 28, 2013, the entire contents of which are incorporated herein by reference.

FIELD

This invention relates to an apparatus for labeled cellular analysis by molecular cytometry.

INTRODUCTION

Mass cytometry is a technique for single cell analysis where cells labeled with metal conjugated antibodies and metallointercalators are introduced individually into an Inductively Coupled Plasma (ICP) ion source, where the cells are vaporized, atomized and ionized for simultaneous elemental analysis. The elemental tags are selected from transitional metals because they are generally absent from biological materials. The numbers of distinguishable tags are therefore limited to the number of available transition elements and the associated metal isotopes. However, it is expected that the need for even greater number of different tags to meet the demands for increasing multi-parameter particle analysis can exceed the number of elemental tags available from transitional metals.

SUMMARY

In view of the foregoing and in accordance with the present teachings, the applicant recognizes that molecular compounds can be designed for labeling particles, such as biological cells, and that by interrogating the corresponding intact molecular ions their physical properties can be used for distinguishing the molecular based tags. In this technique, groups of molecular tags can be released from each particle so that each distinct group of molecular tags can undergo an ionization process that preserves the molecular ions' properties within its group. A flow of each distinct group of molecular ions in successional formation can be interrogated and the molecular ions in each group can be spatially separated according to the properties of each molecular ion. In an analyzer, the presence of each distinct group of molecular ions can be detected by a first detector followed by spatially separating the molecular ions in each group while traversing within a drift tube. A second detector, synchronized to the first detector, detects the separated molecular ions corresponding to each distinct group of molecular ions. The molecular tags can be configured with different releasing properties so that the different molecular tags can be selectively released from the particles as a function of the releasing properties.

DRAWINGS

The skilled person in the art will understand that the drawings, described below, are for illustration purposes only. The drawings are not intended to limit the scope of the applicant's teachings in any way. In the accompanying drawings.

DESCRIPTION OF VARIOUS EMBODIMENTS

Figure 1:
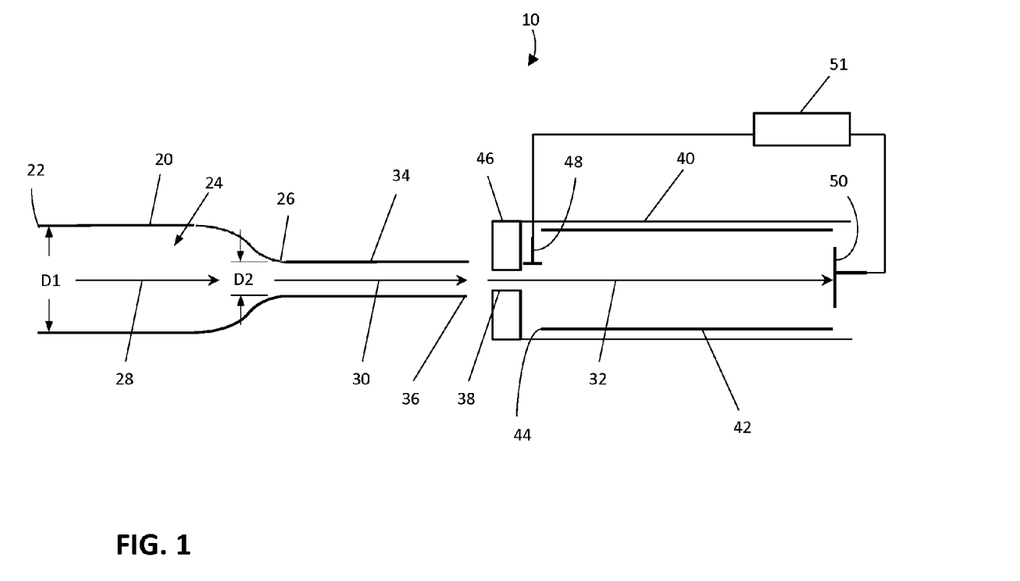
FIG. 1 is a schematic view of a molecular cytometer.

It should be understood that the phrase "a" or "an" used in conjunction with the present teachings with reference to various elements encompasses "one or more" or "at least one" unless the context clearly indicates otherwise. Reference is first made to FIG. 1, which shows a schematic representation of the molecular cytometer, generally indicated by reference number 10. The molecular cytometer 10 comprises a sample delivery system 20 coupled to an ionization source 34 located upstream of an analyzer 40. The sample delivery system 20 can be configured with an inlet section 22 with a transition into an activation region 24. The activation region 24 can be connected to an outlet section 26 for coupling to the ionization source 34, generally operating at atmospheric pressure. The ionization source 34 can be positioned in proximity to the analyzer 40, as indicated in FIG. 1, so that molecular ions can be conducted from the ionization source exit 36 into the analyzer 40 in succession as will be described below. The analyzer 40 can be of the type generally described as a mobility separator having the configuration comprising a drift tube 42 with an upstream section 44 coupled to an ion interface 46. Typically, the analyzer 40 operates at a pressure below atmospheric pressure, about 1-10 Torr for example, in the presence of a drift or buffer gas, and the ion interface 46 can be configured to provide the differential pressure coupling from atmosphere pressure of the ionization source 34 as is generally defined by a differentially pumped systems. Additionally, the analyzer 40 can be equipped with a first detector 48 for detecting the presence of molecular ions prior to their mobility separation and a second detector 50 for detecting the mobility separated molecular ions.

Figure 2:
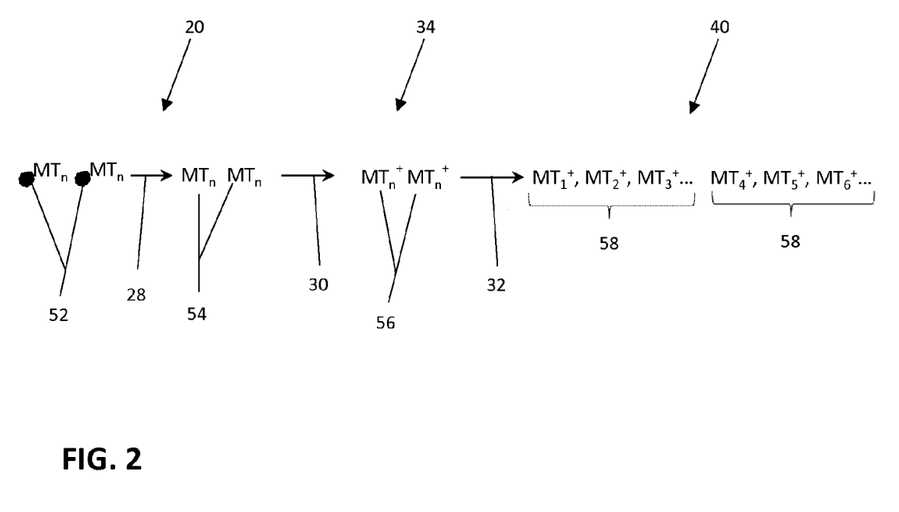
FIG. 2 is a pictorial representation of molecular cytometry showing the events experienced by the molecular tag labeled particles through the molecular cytometer according to FIG. 1.

To help understand how the present combination of the analyzer 40, the ionization source 34 and the sample delivery system 20 can enable the analysis of particles labeled with molecular tags embodied in the present teachings, reference is made to the direction of the flow path or the ion movement generally indicated by the arrows 28, 30, 32. Each arrow 28, 30 and 32 represents the path segments within each of the sample delivery system 20, the ionization source 34 and the analyzer 40 respectively, and additionally, presented here for the purpose of illustrating the various events as will now be described with reference to FIG. 2. For convenience, reference number 52 can be used to indicate the particles labeled with molecular tags in conjunction with the term $MT_n$ to symbolize the various molecular tags attached to the particles. The "n" notation in $MT_n$ can be a variable to signify the different molecular tags or compounds. For example, particles 52 comprising biological cells can be bound to one or more distinct molecular compound, $MT_1, MT_2, MT_3 \ldots$ where each of the molecular compounds $MT_n$ can be configured to have a specific antibody-antigen affinity function for targeted cellular analysis. In multi-parameter analysis, one or more particles can be labeled with many unique molecular tags $MT_n$ and each of the molecular tags $MT_n$ corresponding with each particle can be identified by first releasing the molecular tags $MT_n$ as a group from each particle and then interrogating each group of released molecular tags $MT_n$ as an assemblage. This can be achieved by initially introducing the labeled particles 52 in succession into the sample delivery system 20 through its inlet section 22. Generally, the labeled particles 52 can be suspended in a fluid and transported by a flow stream suitable for maintaining the spatial separation between adjacent particles. The inlet section 22 of the sample delivery system 20 can be configured to provide laminar flow conditions so that the particles are encouraged to maintain their flow in successional formation. Within the sample delivery system 20, the labeled particles 52 can pass through the activation region 24 and the molecular tags $MT_n$ can be released from each particle in accordance with various activation means as will be described below. The groups of molecular tags $MT_n$ released from each of the labeled particles, indicated as numeral 54 in FIG. 2, can remain spatially distinct and can continue to flow in successional formation along the path 28. Accordingly, the internal dimensions of the sample delivery system, generally defined by D1 and D2, can be configured to support laminar flow conditions so to minimize the overlapping between each of the groups of molecular tags 54. For example, in various embodiments, the value for one or both of D1 and D2 can vary so to define the sample delivery system 20 as having an internal taper between the inlet section 22 and the outlet section 26 for maintaining the successional flow formation or orientation of the groups of molecular tags 54.

Subsequently, the ionization source 34 can receive the groups of molecular tags 54 as they appear in succession and, in turn, generate corresponding groups of molecular ions 56. The successional flow stream or pattern within the ionization source 34 can be maintained as required. Under some conditions, the ionization source 34 can be configured to perform the method of soft ionization where the formation of ions can retain their chemical bond structure so that molecular ions can be created from the molecular tags. Consequently, a group of molecular tags 54 previously attached to a particle 52 can be represented by a corresponding group of molecular ions 56 spatially distinct from another group of molecular ions 56. For brevity, the term ions refer to the term molecular ions and each term can be used interchangeably for the present teachings. Following ionization, the groups of ions 56 can be released into the gas phase and can be directed towards the analyzer 40 under the influence of an electrostatic focusing field. The relative position of the ionization source 34 and the analyzer 40 can be aligned to encourage ion transmission into the analyzer 40 while retaining the spatially distinctiveness of each of the groups of ions 56. In various embodiments for example, the path direction 28, 30, 32 depicted in FIG. 1 illustrates that the sample delivery system 20, the ionization source 34 and the analyzer 40 can be axially aligned so that the groups of ions 56 can be delivered directly to the analyzer 40.

While the groups of ions 56 are focused towards the analyzer 40, an aperture 38 in the ion interface 46 can be configured to conduct a flow of the group of ions 56 between the ionization source 34 and the drift tube 42. The dimension of the aperture 38 can be selected for maintaining the differential pressure in the analyzer 56 as noted above. In various embodiments, the ion interface 46 can have multiple apertures for providing different stages of vacuum pressure or the geometry of the aperture 38 can be in the form of a conductance passage or a channel to enable the pressure difference between ionization source 34 and the analyzer 40. Generally, the configuration of the ion interface 46 permits the flow of ions 56 to pass into the drift tube 42 uninterrupted so that each of the groups of ions 56 in the continuous flow can be interrogated by the analyzer 40 as an assemblage.

Figure 3:
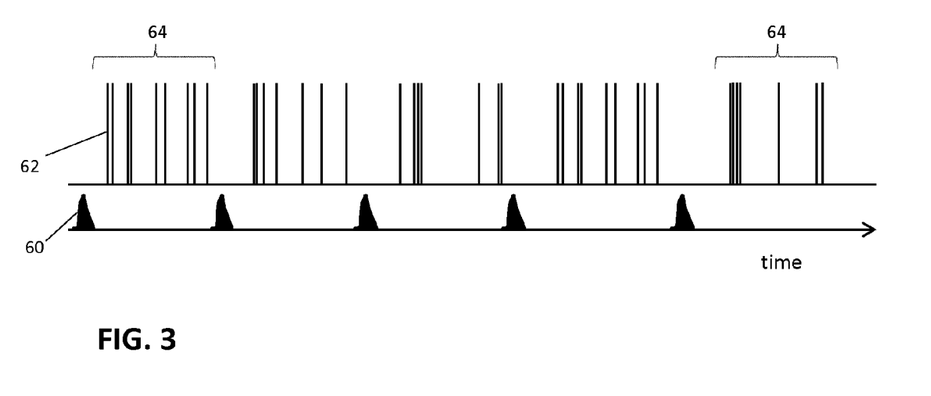
FIG. 3 is an exemplary representation of an analysis containing the signals from the first detector and the second detector according to the present teaching.

Once a group of ions 56 passes through the ion interface 46, the first detector 48, such as a an optical or proximity sensor for example, can be used to detect or sense the presence of the group of ions 56 entering the drift tube 42 prior to mobility separation analysis downstream. The position of the first detector 48 with respect to the path 32 can be chosen to provide non-invasive detection while maintaining non-interference with the ions' movement so that the successive flow of the group of molecular ions 56 corresponding to the group of molecular tags 54 can be preserved. In various embodiments, for example, the first detector 48 can be incorporated into the structure of the ion interface 46 or the ion interface 46 can be adapted to function as a proximity detector. As the group of ions' 56 presence is detected, the first detector 48 can be configured to generate a pulse or signal 60, as indicated in FIG. 3. The temporal spacing of each signal 60 can be used to represent the presence of each group of ions 56 so that each assemblage of mobility separated molecular ions can be associated with its corresponding group of ions 56. For example, after the presence of a group of ions 56 is detected and they are subjected to collisions with a back ground gas in the drift tube, the molecular ions 56 are separated according to their drift time required to reach the second detector 50. Generally, the drift time can be dependent on the molecular ion's mobility (drift velocity) which can be based on their size and shape as is typically related to the collision cross-section of the molecule. The second detector 50 located downstream of the first detector 48 can detect the arrival of the separated molecular ions 58 and produce a representative temporal signal 62 for each of the arriving separated ions 58. The signal 60 from the first detector 48 can be used as a trigger for the second detector 50 in such a way as to coordinate, with a synchronizer 51 for example, the arrival times of a group of mobility separated ions 58 represented as an assemblage 64 of signals 62 and to associate them with the presence of that group of ions 56. In general terms, the synchronizer can be used to coordinate the second detector 50 with the first detector 48 so that the assemblage 64 of signals 62 are related to the group of ions 56 previously detected. Therefore, each of the groups of mobility separated molecular ions 58 can be correspondingly associated with the each of the groups of molecular ions 56 which represents the groups of molecular tags 54 labeled on each particle 52.

While the present teachings are described in conjunction with various embodiments, it is not intended that the present teachings be limited to such embodiments. On the contrary, the present teachings encompass various alternatives, modifications, and equivalents, as will be appreciated by those of skill in the art. For example, the present applicants recognize that the second detector 50, such as a Faraday cup type detector, can be operated in a continuous acquisition mode for recording the arrival of each separated molecular ion as they appear based on their drift time through the drift tube. In some embodiments, this can be accomplished by monitoring the electric current resulting from ions striking the Faraday cup (or plate) and observing the temporal presence of each current spike or peak. A recording of the drift times as a function of the trigger signals 60 can be evaluated either during the acquisition or offline at a later time, using a processor for example, to identify the groups of separated molecular ions 58 with the corresponding groups of molecular ions 56. Alternatively, the second detector 50 can be triggered intermittently so that it operates for a specified duration upon receiving a signal 60 from the first detector 48. The specified duration can be dependent on the range of molecular tags corresponding with the expected collisional cross-section of the molecules.

Furthermore, although the temporal signals 62 shown in FIG. 3 are represented by vertical lines with the same heights, the temporal signals 62 can be characterized by peaks of varying intensities. The number of separated molecular ions 58 with the same mobility, thus arriving concurrently, can be detected by the second detector 50 such that the detector 50 can generate peaks with corresponding intensities that is a representative of this number. In various embodiments, the assemblage 64 of temporal signals 62 with varying intensities can be used for quantitative analysis of each group of molecular ions 56 identified by the first detector 48. The particles 52 can be labeled with or coexist with a preselected molecule tag $MT_n$ that can be used to represent a reference standard for use as a means of intensity and or mobility calibration. The calibration feature is advantageous in qualitative and quantitative analysis. Furthermore, as indicated in FIG. 3 the time spacing between successive signal 60, and the corresponding assemblage 64, can be regular or irregular and can generally depend on the spatial separation between the labeled particles 52, between the molecular tags 54, and between the molecular ions 56.

In various embodiments, the molecular compounds that can be used in the molecular tags $MT_n$ can be volatile compounds selected from generally known complexes or they can be synthesized from building blocks of small molecules to provide an array of tags having distinguishable molecular ions capable of analysis by mobility separation. Generally, volatile molecular compounds that can transition to the gas phase at ambient temperatures or to be vaporized at an elevated temperature, can be used. In some instances, the volatile molecular compound can be selected from the various families comprising molecular metal clusters, organic polymers and polymer-based elemental complexes to name a few. Moreover, both inorganic and organic compounds, such as diatomic lanthanides and benzene derivatives and other hydrocarbons can be considered for use in the molecular tags $MT_n$. Typically, the molecular tags $MT_n$ can comprise a linker for attaching to the complex. The linker can be chosen with properties suitable for binding to a particle of interest directly or through an intermediary such as a biomolecule exhibiting antibody-antigen affinity or other binding affinity attributed with various affinity reagents for example.

Additionally, the linker can be selected according to its attachment stability and according to the conditions required for breaking the bond between itself and the molecular tags $MT_n$ or between itself and the labeled particles 52 for the purpose of releasing the molecular tags $MT_n$. Generally, many releasable linkers can be considered for joining the molecular tags 54 to the particles and, under certain reactive conditions provided by the activation agent, the linker can be cleaved. For example, releasable linkers can be selected from the cleavable groups comprising phosphotriester, phenacyl ester, disulfide bridges and phospholipids to name a few. Other suitable cleavable groups and their corresponding cleavage conditions can be considered for the present teaching. In various embodiments for example, the linker can be a photo-cleavable linker where the breakage of a photosensitive bond can be activated by the presence of a specific wave length of light. In this instance, the photon activating property of the wave length specific light can be considered the activation agent. Alternatively, other activation properties by chemical activation such as enzymes, reducing agents and oxidation agents; by thermal energy activation through conduction, convection or radiation; or by other physical activation employing direct or indirect energetic wave transmission can be considered for releasing the molecular tags $MT_n$ from the labeled particles 52. The process for releasing the molecular tags $MT_n$, however, is not limited only to the process of breaking the bond associated with the linker for cleaving off the cell. For instance, molecular tags $MT_n$ that have been labeled on a biological cell can be released by a chemical activation through the introduction of a detergent-based buffer. The detergent can cause cell disruption that would effectively release the molecular tags $MT_n$. Subsequently, the cell lysate, which includes the released groups of molecular tags 54, can be transferred in its entirety to the ionization source for producing the groups of molecular ions 56. An additional step involving separating the released tags from the cell lysate or from the cleaved off cells prior to ionization can be performed, as described below, but can likely be unnecessary since the analysis would generally target those molecular ions associated with the molecular tags $MT_n$. Moreover, since the mobility separation analysis of the present teachings is configured with the dual detectors 48, 50 the specificity between the detected groups of ions 56 and the mobility separated molecular ions 58, can render any contribution from non-molecular tags as background noise. However, in various embodiments, the perceived background noise can undergo further deciphering or analysis for obtaining information regarding the content of the cell lysate.

In various embodiments, after releasing the molecular tags $MT_n$ from the labeled particles there can be some advantages for separating out the particles or the lysate prior to the ionization. In this instance, a liquid phase separation method can be considered. For example, a chromatograph column can be positioned between the outlet section 26 of the sample deliver system 20 and the ionization source 34 in order to retain the cells or lysate during analysis of the molecular tags 54. Alternatively, a flow diverter can be connected to or integrated with the sample delivery system 20 to provide two distinct flow paths, one for the particles and one for the released molecular tags $MT_n$. The path for the tags can be connected to the ionization source while the path for the particles can be configured for discharge or for further particle analysis. Additional flow paths can be employed to provide further particle or lysate separation as required.

Furthermore, in various embodiments, the particles can be separated from the released molecular tags in the gas phase. For example, the ionization source 34 can receive groups of released molecular tags 54 that include the particles and can subsequently generate groups of molecular ions 56 and charged particles. While in the gas phase, the charged particles can be attracted or diverted by using, for example, an electrostatic field or gas dynamic flow or a combination thereof. The diverted charged particles can be discarded or they can undergo analysis by additional techniques as is known for charged particle analysis.

Alternatively, in various embodiments, the molecular tags $MT_n$ can be encapsulated in a structure comprising a hydrogel microparticle, such as the thermo-responsive microgel-based material poly(N-isopropylacrylamide) for example. The microgel material can be functionalized for bonding to the particles as required. The molecular tags $MT_n$ can be released directly from the particles into the gas phase by thermal contact with a hot surface or by irradiative conduction/convection to evaporate part or all of the microgel material. The molecular tags $MT_n$ released into the gas phase along with any remnants associated with the particles and microgel can be expelled or ionized by an ionization source 34 suitable for gas phase soft ionization as will be described below.

Generally, the activation agents can be introduced into the activation region 24 for exposure to the labeled particles 52 by various means. For example, a chemical activation agent comprising the lysing buffer can be delivered into the activation region 24 as a liquid with flow dynamics configured for optimizing cell interaction while minimizing the effects that can interfere with the successive formation of the released groups of molecular tags 54. In this instance, the flow of liquid activation agent can be introduced in a concentric or parallel pattern for contacting the flow of labeled particles 52. Alternatively, some noncontact activation agents, such as UV light or thermal energy irradiation, can be transmitted into the activation region 24 through an optical port in the sample delivery system 20. Other consideration for physical or radiating activation agents can include sound wave propagation such as ultrasound emission or other non-ionizing radiation like microwaves to name a few. As the labeled particles 52 passes through the activation region 24, the particles can be exposed to the activation agent and the interaction can cause the molecular tags 54 to be released. In various embodiments, upon exposure to the activation agent, the release can occur immediately or the release can occur during a predetermined period of time as is required to enable a timed delayed release of molecular tags 54. Typically, the timed delay release can be a function of the releasing properties of the linker or as a function of the concentration or makeup of the agent. The geometry of the activation region 24, the length for example, can be configured to accommodate for the timed delayed release as required.

Additionally, in various embodiments, the release of the molecular tags 54 from the labeled particles 52 is not limited to within the activation region 24 but can occur at various areas along the paths 28, 30 between the inlet section 22 and the exit 36 of the ionization source 34. For example, in some instances, different types of particles under consideration can have physical characteristics that can disrupt the flow dynamics or can have no or limited influence by the flow stream configured for maintaining the spatial separation between adjacent particles within the system 20. This can result in erroneous data where some of the labeled particles 52 flowing in a non-succession formation can reduce the capability of the analyzer 40 to resolve the separated molecular ions 58 within overlapping groups of molecular ions 56. Consequently, additional time for the particle move within the flow stream, either within the sample delivery system 20 or within the ionization source 34, can be required to develop sufficient spacing between the labeled particles. In this instance, it can be an advantage to delay releasing some of the molecular tags until the labeled particles fall into succession formation further downstream of the sample delivery system 20. Accordingly, the timed delayed release as described above can be incorporated as one of multiple releases of different releasable linkers having different releasing properties. Furthermore, different activation agents that are specific to the different linkers can be directed to the flow of labeled particles at various locations along the paths 28, 30. In this arrangement, the particles can be labeled with molecular tags with different releasable linkers so that the different types of molecular tags can be release according to the type of particles under consideration. In various embodiments, the releasing agent's introducing location can be adjustable as a means of tuning the resolution between the groups of separated molecular ions 58.

Figure 4:
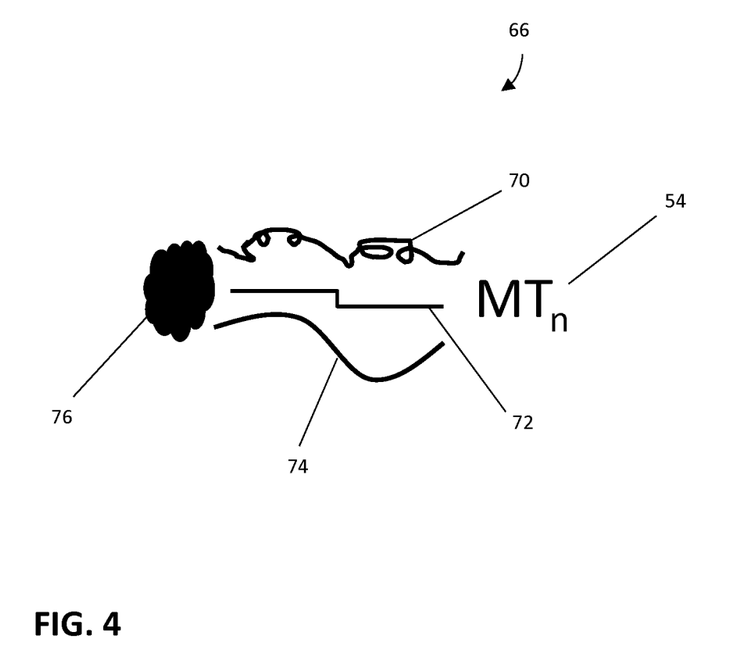
FIG. 4 is a pictorial representation of a molecular tag labeled particle suitable for use in molecular cytometry according to the present teaching.

While a releasable linker of a single type can be chosen to join each molecular tag 54 to a particle 52, in various embodiments, more than one different type of releasable linkers (multiple linkers) can be attached simultaneously to a molecular tag 54 to form a particle labeled with multiple linker molecular tag 66 as depicted in FIG. 4. In this illustration, different types of releasable linkers 70, 72, 74 can be attached to the same molecular tag $MT_n$ so that each releasable linker 70, 72, 74 can join the same molecular tag $MT_n$ to the same type of particle 76. As previously described, the different releasable linkers 70, 72, 74 can be bound to the particle 76 directly or through an intermediary such as an antibody or other affinity reagents that are specific to the each particle type of interest. Each of the different releasable linkers 70, 72, 74 can be characterized by their different releasing properties and, accordingly, by their different activation requirements. Consequently, releasing the molecular tag 54 from the labeled particle 66 can require a combination of different activation agents sympathetic to each of the different linkers. While in this illustration the molecular tag is described as having three different types of releasable linkers, the number of different releasable linkers can typically be more than one to provide multiple permutations. In this fashion, molecular tags $MT_n$ can be encoded according to the combination of different releasable linkers and subsequently selectively released by the different combination releasing agents and analyzed by the molecular cytometer 10 in FIG. 1.

The size and composition of the molecular tags $MT_n$ can be chosen in accordance with its volatility and capability of producing corresponding molecular ions 58 by the method of soft ionization, as described above. Corollary, the choice of soft ionization method can depend on the nature of the molecular tags and the mass range of the analyzer to perform its mobility separation effectively. In various embodiments, for example, the soft ionization methods of fast atom bombardment (FAB) can accommodate a large variety of compounds typically with molecular weights from 300 to 6000 Da; electrospray ionization (ESI) is suitable for molecular tags up to about 20,000 Da; atmospheric pressure chemical ionization (APCI) and field ionization (FI) can be effective for compounds unable to be ionized by ESI for up to 2,000 Da; and laser desorption ionization (LDI) can potentially handle large molecules up to 100,000 Da. Accordingly, in various embodiments, the analyzer can be configured as a mobility separator with the capability of separating molecular ions with a range of molecular weights between about 100 and 100,000 Da. Alternatively, the mobility separator can be configured for the separation of particular molecular ions with a molecular weight range between 1000 and 10,000 Da.

Although the analyzer has been described with respect to the mobility separator operating at a typical pressure between 1 and 10 Torr, in some instances the present teachings can incorporate mobility separators operating at higher pressures. In various embodiments, for example, the mobility separator can be configured for atmospheric pressure conditions, approximately 760 Torr, and at an elevated temperature where required. Consideration can be given to other types of mobility based systems such as those define by differential mobility spectrometry (DMS) or differential mobility analyzer (DMA) utilizing gas dynamics for causing ions of different mobility to experience different trajectories.

What is claimed is:

1. A molecular cytometer for the analysis of particles labeled with molecular tags comprising:
    a sample delivery system for receiving the particles labeled with molecular tags, the sample delivery system being adapted to deliver groups of molecular tags released from the particles;
    an ionization source coupled to the sample delivery system, the ionization source configured for generating groups of molecular ions corresponding to the groups of molecular tags; and
    an analyzer comprising:
    an ion interface for conducting a flow of the groups of molecular ions;
    a drift tube having an upstream section positioned to receive the flow of the groups of molecular ions from the ion interface, the drift tube configured for mobility separation of the molecular ions in each of the groups of molecular ions;
    a first detector positioned to detect the presence of each of the groups of molecular ions received by the drift tube; and
    a second detector configured for detecting the mobility separated molecular ions associated with the presence of each of the groups of molecular ions.

2. The molecular cytometer according to claim 1 in which the groups of molecular ions in the flow is conducted in succession.

3. The molecular cytometer according to claim 2 in which the ion interface continuously conducts the flow of the groups of molecular ions to the drift tube.

4. The molecular cytometer according to claim 1 further comprising a synchronizer being adapted to coordinate the first detector and the second detector.

5. The molecular cytometer according to claim 1 in which the sample delivery system further comprises an activation region for releasing the molecular tags from each of the particles into corresponding groups of molecular tags.

6. The molecular cytometer according to claim 5 in which the activation region is adapted to receive an activation agent for releasing molecular tags from each of the particles, the activation agent comprising an activation property selected from photon, thermal, chemical, physical, or a combination thereof.

7. The molecular cytometer according to claim 1 in which the second detector is positioned downstream of the first detector.

8. The molecular cytometer according to claim 1 in which the ionization source is a soft ionization source.

9. The molecular cytometer according to claim 8 in which the ionization source is selected from an electrospray ionization source, a chemical ionization source, an electron ionization source, laser desorption ionization source, and a field ionization source.

10. A molecular cytometer comprising:
    a sample delivery system;
    an ionization source coupled to the sample delivery system configured for generating groups of molecular ions; and
    an analyzer comprising:
    an ion interface for conducting a flow of the groups of molecular ions;
    a drift tube having an upstream section positioned downstream of the ion interface to receive the flow of the groups of molecular ions, the drift tube configured for mobility separation of molecular ions;
    a first detector positioned at the upstream section of the drift tube to detect the presence of each of the groups of molecular ions received by the drift tube; and
    a second detector positioned downstream of the first detector, the second detector configured for detecting the mobility separated molecular ions associated with the presence of each of the groups of molecular ions.

11. The molecular cytometer according to claim 10 further comprising a synchronizer being adapted to coordinate the first detector and the second detector.

12. The molecular cytometer according to claim 11 in which the ionization source is a soft ionization source.

13. The molecular cytometer according to claim 12 in which the ionization source is selected from an electrospray ionization source, a chemical ionization source, an electron ionization source, laser desorption ionization source, and a field ionization source.

14. A method of molecular cytometry for the analysis of particles labeled with molecular tags comprising:
    receiving the particles labeled with molecular tags;
    releasing the molecular tags from each of the particles to form corresponding groups of molecular tags;
    ionizing the molecular tags in each of the groups of molecular tags to form corresponding groups of molecular ions;
    separating the molecular ions in each of the groups of molecular ions as a function of collisional cross-section; and
    detecting the separated molecular ions corresponding with each of the groups of molecular ions.

15. The method according to claim 14 in which the particles labeled with molecular tags are in successional formation.

16. The method according to claim 15 further comprising detecting the presence of each of the groups of molecular ions corresponding with each of the groups of molecular tags.

17. The method according to claim 16 in which detecting the separated molecular ions is triggered by detecting the presence of each of the groups of molecular ions.

18. The method according to claim 15 further comprising directing an activation agent to the flow of particles labeled with molecular tags for releasing the molecular tags.

19. The method according to claim 18 in which the activation agent comprises an activation property selected from photon, thermal, chemical, physical, or a combination thereof.

20. The method according to claim 14 in which the ionizing is performed by a method of soft ionization.

* * * * *